US009384540B2

(12) United States Patent
Orschel

(10) Patent No.: US 9,384,540 B2
(45) Date of Patent: Jul. 5, 2016

(54) SYSTEMS AND METHODS FOR INTERFEROMETRIC PHASE MEASUREMENT

(71) Applicant: SunEdison Semiconductor Limited (UEN201334164H), St. Peters, MO (US)

(72) Inventor: Benno Orschel, St. Louis, MO (US)

(73) Assignee: SunEdison Semiconductor Limited (UEN201334164H), Singapore (SG)

( * ) Notice: Subject to any disclaimer, the term of this patent is extended or adjusted under 35 U.S.C. 154(b) by 230 days.

(21) Appl. No.: 14/095,624

(22) Filed: Dec. 3, 2013

(65) Prior Publication Data

US 2015/0153166 A1 Jun. 4, 2015

(51) Int. Cl.
H04N 7/18 (2006.01)
G06K 9/00 (2006.01)
G06T 7/00 (2006.01)
G01B 9/02 (2006.01)
G01N 21/88 (2006.01)

(52) U.S. Cl.
CPC ............ G06T 7/0004 (2013.01); G01B 9/0201 (2013.01); G01B 9/02084 (2013.01); G01N 21/88 (2013.01)

(58) Field of Classification Search
CPC .................. G06T 7/0004; G06T 2207/10016; G06T 2207/30108; H04N 5/2256
See application file for complete search history.

(56) References Cited

U.S. PATENT DOCUMENTS

| 7,019,815 | B2 | 3/2006 | Jasper et al. |
| 7,324,917 | B2 | 1/2008 | Koliopoulos et al. |
| 8,605,983 | B2* | 12/2013 | Weston ................ G01B 11/007 348/48 |
| 8,768,665 | B2 | 7/2014 | Veeraraghavan et al. |
| 2006/0023571 | A1* | 2/2006 | Uebo ..................... G01S 13/887 367/101 |
| 2006/0045313 | A1* | 3/2006 | Gao ....................... G01B 11/002 382/106 |
| 2009/0036772 | A1* | 2/2009 | Lu ......................... G01S 7/52046 600/437 |
| 2012/0140239 | A1 | 6/2012 | Lee et al. |
| 2014/0071239 | A1* | 3/2014 | Yokota ................... G01B 11/25 348/45 |

FOREIGN PATENT DOCUMENTS

| EP | 1521122 A1 | 6/2005 |
| JP | 3632078 B2 | 3/2005 |
| WO | 2010025334 A2 | 3/2010 |

OTHER PUBLICATIONS

Valley, John et al., Approaching New Metrics for Wafer Flatness: An Investigation of the Lithographic Consequences of Wafer Non-Flatness, SPIE Proceedings, May 24, 2004, vol. 5375, Metrology, Inspection and Process Control for Microlithography XVIII, 11 pgs.

* cited by examiner

Primary Examiner — Heather Jones
Assistant Examiner — Tsion B. Owens
(74) Attorney, Agent, or Firm — Armstrong Teasdale LLP

(57) ABSTRACT

A method for measuring phase shift to detect irregularities of a surface is described. Additionally, a system for measuring phase shift to detect irregularities of a surface is provided. Further, a non-transitory computer-readable storage medium having computer-executable instructions embodied thereon is described. The computer-executable instructions are for measuring phase shift to detect irregularities of a surface.

20 Claims, 6 Drawing Sheets

SYSTEMS AND METHODS FOR INTERFEROMETRIC PHASE MEASUREMENT

BACKGROUND

The field relates generally to phase measurement, and more particularly to systems and methods for interferometric phase measurement using a Fourier transform.

Some known systems and methods for performing interferometric phase measurement include taking a series of images at different phase shifts and then numerically estimating, from the images, a cosine and sine of the phase of each image from the tangent in each pixel. From the numerically-estimated cosine and sine, the phase is then determined by calculating an arctangent. More specifically, the known systems and methods involve numerically stepping through one full phase in small steps and taking fringe images, then using the fringe images to perform a Fourier transformation through phases of a phase-dependent fringe intensity. Resulting first order sine and cosine coefficients give the tangent value, from which then the phase is determined by calculating the arctangent. However, this solution is impractical because it requires significant time to take the images, and requires a significant amount of processing time.

Some known systems and methods reduce image capture time and processing time by taking a reduced number of fringe images. However, such systems and methods have reduced numerical accuracy and are less effective at rejecting erroneous data resulting from noise and/or vibration.

BRIEF DESCRIPTION

In one aspect, a method for measuring phase shift to detect irregularities of a surface is provided. The method is implemented with a camera, a computing device coupled to or within the camera, a light source, a surface disposed opposite the light source, a semi-reflective reference plane disposed between the light source and the surface, and a beam splitter disposed between the light source and the reference plane. The light source emits a light beam comprising a first portion and a second portion, wherein the first portion is reflected by the reference plane and the second portion is transmitted through the reference plane and reflected by the surface. The beam splitter directs the reflected first portion and the reflected second portion to the camera. The method includes generating a first image by exposing the camera to the first portion and the second portion of the light beam while translating the reference plane along a distance between the surface and the beam splitter at a first phase sweep rate. The method additionally includes generating a second image by exposing the camera to the first portion and the second portion of the light beam while translating the reference plane along the distance at a second phase sweep rate. Additionally, the method includes generating a third image by exposing the camera to the first portion and the second portion of the light beam while translating the reference plane along the distance at a third phase sweep rate. Further, the method includes generating, by the computing device, a first Fourier transform image and a second Fourier transform image based on the first image, the second image, and the third image. Additionally, the method includes generating, by the computing device, a phase image based on the first Fourier transform image and the second Fourier transform image.

In another aspect, a system for measuring phase shift to detect irregularities of a surface is provided. The system includes a camera, a computing device coupled to or within the camera, a light source, a surface disposed opposite the light source, a semi-reflective reference plane disposed between the light source and the surface, and a beam splitter disposed between the light source and the reference plane. The light source emits a light beam that includes a first portion and a second portion. The first portion is reflected by the reference plane and the second portion is transmitted through the reference plane and reflected by the surface. The beam splitter directs the reflected first portion and the reflected second portion to the camera. The system is configured to generate a first image by exposing the camera to the first portion and the second portion of the light beam while translating the reference plane along a distance between the surface and the beam splitter at a first phase sweep rate. The system is additionally configured to generate a second image by exposing the camera to the first portion and the second portion of the light beam while translating the reference plane along the distance at a second phase sweep rate. Additionally, the system is configured to generate a third image by exposing the camera to the first portion and the second portion of the light beam while translating the reference plane along the distance at a third phase sweep rate. The system is also configured to generate a first Fourier transform image and a second Fourier transform image based on the first image, the second image, and the third image, and generate a phase image based on the first Fourier transform image and the second Fourier transform image.

In another aspect, a non-transitory computer-readable storage medium having computer-executable instructions embodied thereon is provided. The computer-executable instructions are for measuring phase shift to detect irregularities of a surface in a system including a camera, a computing device coupled to or within the camera, a light source, a surface disposed opposite the light source, a semi-reflective reference plane disposed between the light source and the surface, and a beam splitter disposed between the light source and the reference plane. The light source emits a light beam that includes a first portion and a second portion. The first portion is reflected by the reference plane and the second portion is transmitted through the reference plane and reflected by the surface. The beam splitter directs the reflected first portion and the reflected second portion to the camera. When executed by the computing device, the computer-executable instructions cause the computing device to generate a first image by exposing the camera to the first portion and the second portion of the light beam while translating the reference plane along a distance between the surface and the beam splitter at a first phase sweep rate. The computer-executable instructions additionally cause the computing device to generate a second image by exposing the camera to the first portion and the second portion of the light beam while translating the reference plane along the distance at a second phase sweep rate, generate a third image by exposing the camera to the first portion and the second portion of the light beam while translating the reference plane along the distance at a third phase sweep rate, generate a first Fourier transform image and a second Fourier transform image based on the first image, the second image, and the third image, and generate a phase image based on the first Fourier transform image and the second Fourier transform image.

DETAILED DESCRIPTION

Figure 1:
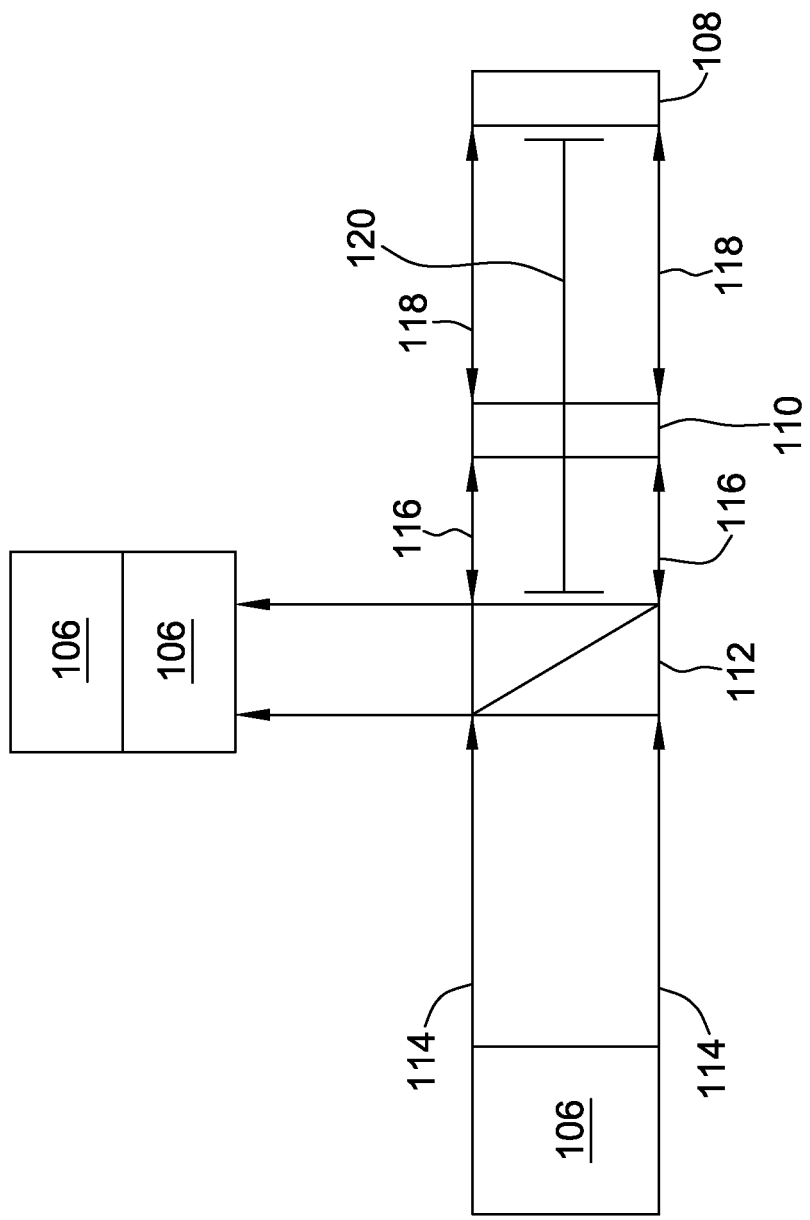
FIG. 1 is a diagram of an example system for measuring phase shift to detect irregularities on a surface.

FIG. 1 is a diagram of a system 100 for measuring phase shift to detect irregularities on a surface. System 100 includes a camera 102, and a computing device 104 that is coupled to camera 102. In other implementations, computing device 104 is included within camera 102. System 100 additionally includes a light source 106 and a surface 108 that is disposed opposite light source 106. Surface 108 may be a surface of any object for which surface irregularities are to be measured. For example, surface 108 may be a surface of a silicon wafer. A semi-reflective reference plane 110 is disposed between light source 106 and surface 108. Additionally, a beam splitter 112 is disposed between light source 106 and semi-reflective reference plane 110. During operation of system 100, light source 106 emits a light beam 114. Light beam includes a first portion 116 and a second portion 118. First portion 116 is reflected by semi-reflective reference plane 110. Second portion 118 is transmitted through semi-reflective reference plane 110 and reflected by surface 108. Beam splitter 112 directs reflected first portion 116 and second portion 118 to camera 102 for imaging.

Figure 2:
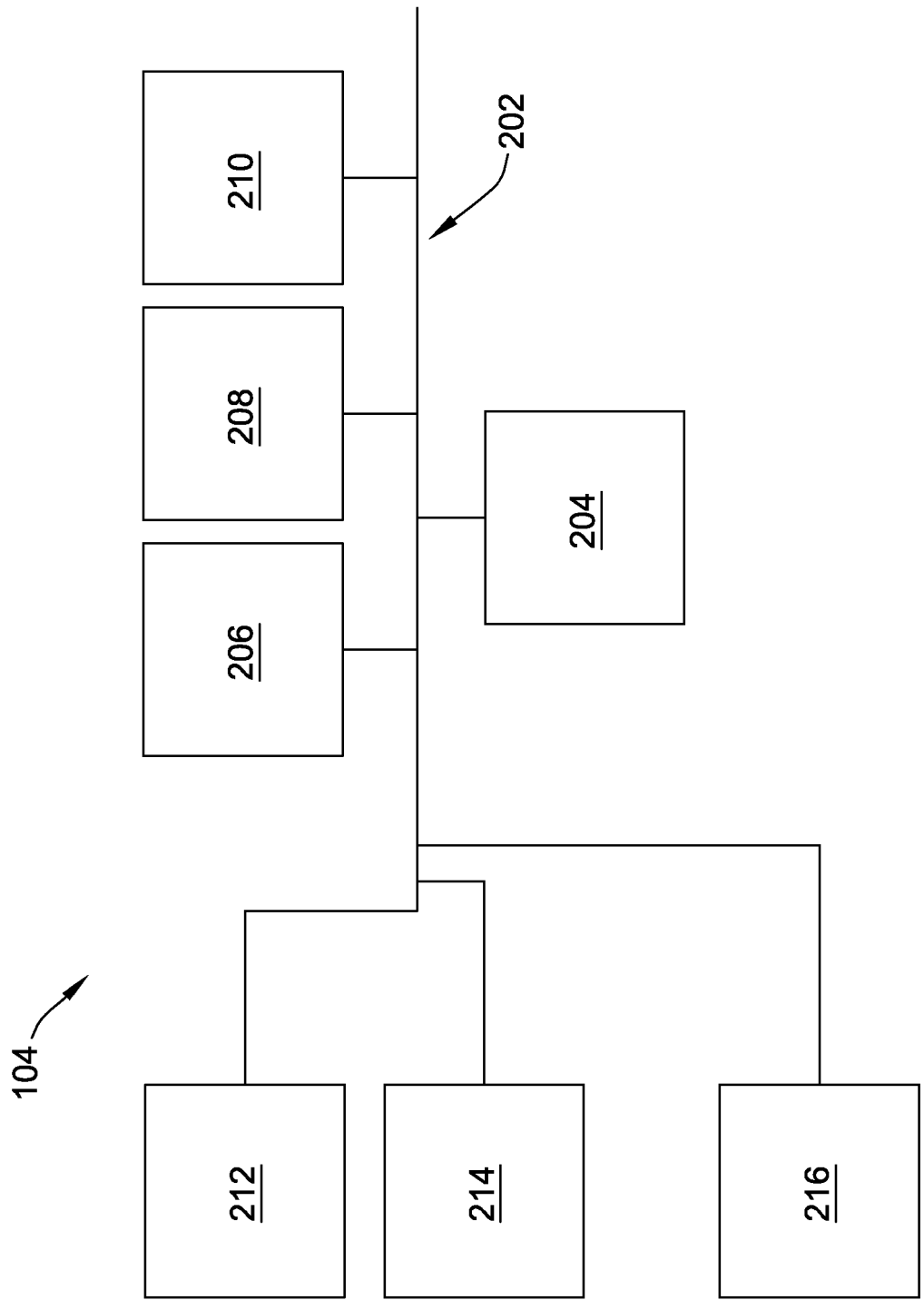
FIG. 2 is a block diagram of an example computing device that may be used in the system of FIG. 1.

FIG. 2 is a schematic diagram of computing device 104. Computing device 104 may include a bus 202, a processor 204, a main memory 206, a read only memory (ROM) 208, a storage device 210, an input device 212, an output device 214, and a communication interface 216. Bus 202 may include a path that permits communication among the components of computing device 200.

Processor 204 may include any type of conventional processor, microprocessor, or processing logic that interprets and executes instructions. Main memory 206 may include a random access memory (RAM) or another type of dynamic storage device that stores information and instructions for execution by processor 204. ROM 208 may include a conventional ROM device or another type of static storage device that stores static information and instructions for use by processor 204. Storage device 210 may include a magnetic and/or optical recording medium and its corresponding drive.

Input device 212 may include a conventional mechanism that permits computing device 104 to receive commands, instructions, or other inputs from a user, including visual, audio, touch, button presses, stylus taps, etc. Accordingly, input device 212 may include, for example, a microphone, one or more buttons, and/or a touch screen. Output device 214 may include a conventional mechanism that outputs information to the user, including a display (including a touch screen) and/or a speaker. Communication interface 216 may include any transceiver-like mechanism that enables computing device 104 to communicate with other devices and/or systems. For example, communication interface 216 may include mechanisms for communicating with another device, such as camera 102. As described above, in some implementations, computing device 104 is included within camera 102.

As described herein, computing device 104 performs operations to facilitate measuring phase shift to detect irregularities in surface 108 (FIG. 1). Computing device 104 may perform these and other operations in response to processor 204 executing software instructions contained in a computer-readable medium, such as memory 206. A computer-readable medium may be defined as a physical or logical memory device and/or carrier wave. The software instructions may be read into memory 206 from another computer-readable medium, such as data storage device 210, or from another device via communication interface 216. The software instructions contained in memory 206 may cause processor 204 to perform processes described herein. In other implementations, hardwired circuitry may be used in place of or in combination with software instructions to implement processes consistent with the subject matter herein. Thus, implementations consistent with the principles of the subject matter disclosed herein are not limited to any specific combination of hardware circuitry and software.

Figure 3:
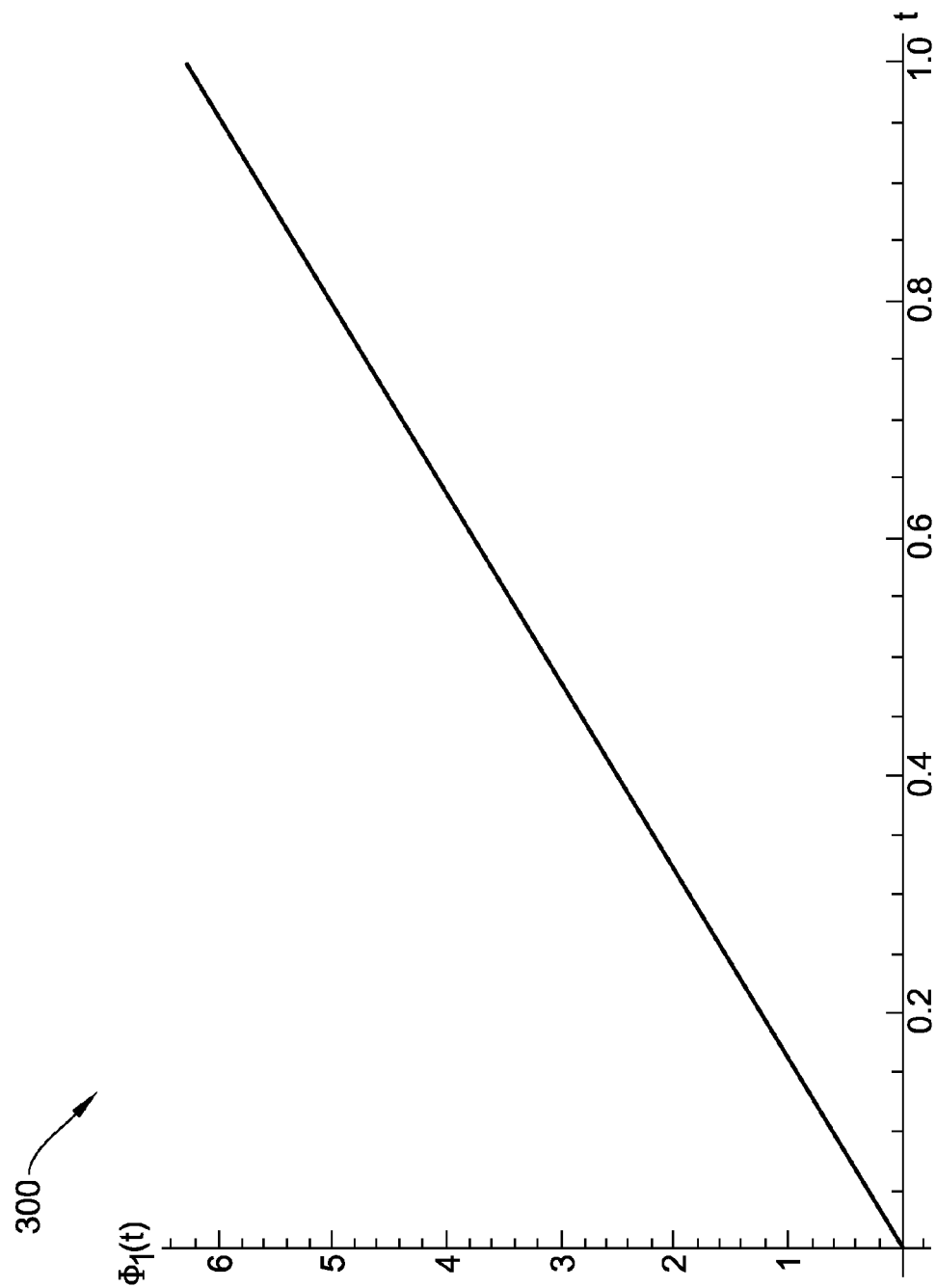
FIG. 3 is a plot of phase versus time during a first exposure performed by the system of FIG. 1.

System 100 exposes camera 102 three times, each time accumulating a phase-dependent fringe intensity while a phase sweeps through $2\pi$ radians or a multiple of $2\pi$ radians. FIG. 3 is a plot 300 of a phase versus time during a first exposure performed by system 100 (FIG. 1). The rate of the sweep of the phase is constant during the first exposure, thereby enabling camera 102 to linearly accumulate a phase-dependent fringe intensity. The rate of the first phase sweep is given by Equation 1.

$$\Phi'_1 = 2\pi \quad \text{(Equation 1)}$$

Figure 4:
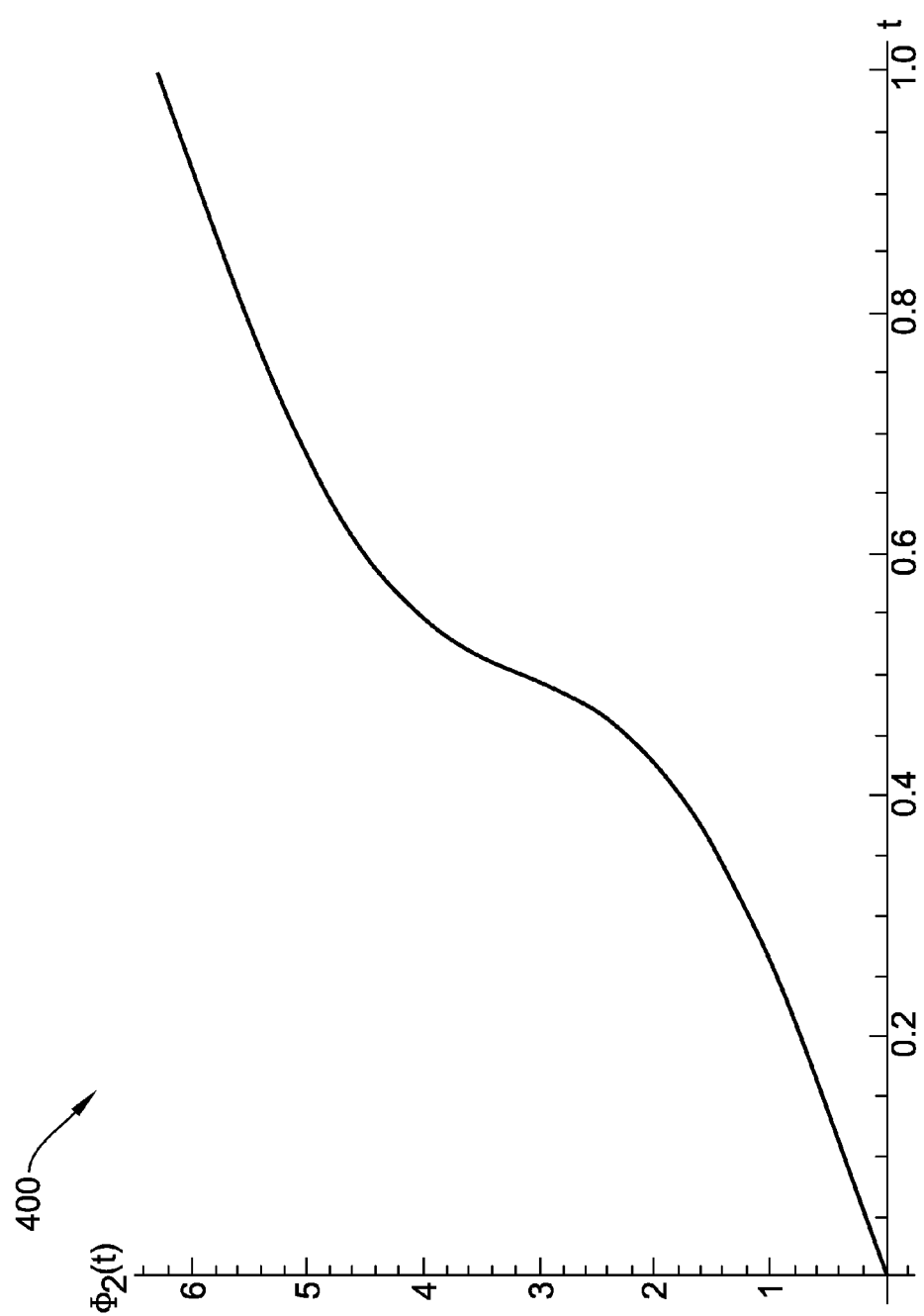
FIG. 4 is a plot of phase versus time during a second exposure performed by the system of FIG. 1.

FIG. 4 is a plot 400 of phase versus time during a second exposure performed by system 100 (FIG. 1). The rate of a second sweep of the phase is controlled such that an accumulated phase-dependent fringe intensity during the second exposure is substantially the same as during the first exposure plus an equivalent of a first order cosine Fourier transform over the phase of the phase-dependent fringe intensity. The rate of the second phase sweep is given by Equation 2, wherein $\xi$ is a modulation coefficient with a value of, for example, approximately 0.75, and $\Phi$ represents the phase.

$$\Phi'_2 = 2\pi/(1+\xi\cos(\Phi)) \quad \text{(Equation 2)}$$

Figure 5:
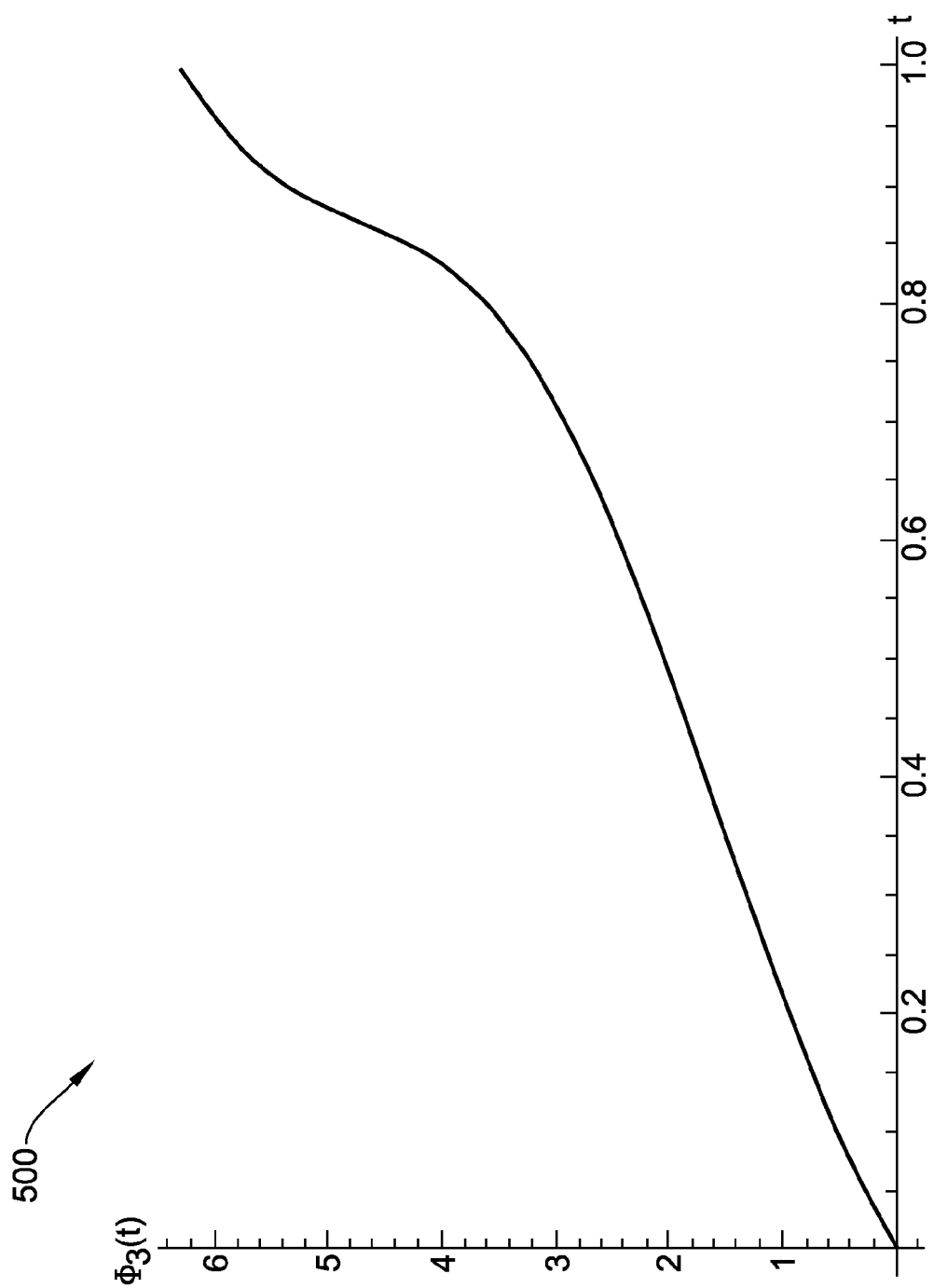
FIG. 5 is a plot of phase versus time during a third exposure performed by the system of FIG. 1.

FIG. 5 is a plot 500 of phase versus time during a third exposure performed by system 100 (FIG. 1). During the third exposure, the rate of a third sweep is controlled such that an accumulated phase-dependent fringe intensity during the third exposure is substantially the same as during the first exposure, plus an equivalent of a first order sine Fourier transform over the phase of the phase-dependent fringe intensity. The rate of the third phase sweep is given by Equation 3, wherein $\xi$ is a modulation coefficient with a value of, for example, approximately 0.75, and $\Phi$ represents the phase.

$$\Phi'_3 = 2\pi/(1+\xi\sin(\Phi)) \quad \text{(Equation 3)}$$

After the three phase sweeps and corresponding three exposures occur, as described above, memory 206 of computing device 104 includes pixel values for each of the three exposures. In other words, memory 206 contains, for each of the three exposures, a corresponding image. The pixel values of the first image, the second image, and the third image corresponding to the first exposure, the second exposure, and the third exposure are given by Equations 4, 5, and 6. In Equations 4, 5, and 6, Y is a pixel value at coordinates x and y, I is the phase-dependent fringe intensity, t is time, $\Phi$ is the phase, and $\Phi'$ is the first derivative of the phase with respect to time (i.e., the phase sweep rate).

$$Y_1(x,y) = \int I(x,y, \Phi1(t))dt = \int I(x,y, \Phi1(t))/\Phi'1(t)d\Phi \quad \text{(Equation 4)}$$

$$Y_2(x,y) = \int I(x,y, \Phi2(t))dt = \int I(x,y, \Phi2(t))/\Phi'2(t)d\Phi \quad \text{(Equation 5)}$$

$$Y_3(x,y) = \int I(x,y, \Phi3(t))dt = \int I(x,y, \Phi3(t))/\Phi'3(t)d\Phi \quad \text{(Equation 6)}$$

Based on Equations 4, 5, and 6, the first image, the second image, and the third image can be expressed as Equations 7, 8, 9, respectively, as follows:

$$Y_1(x,y)=1/2\pi \int I(x,x,\Phi)d\Phi \quad \text{(Equation 7)}$$

$$Y_2(x,y)=1/2\pi \int I(x,x,\Phi)(1+\xi\cos(\Phi))d\Phi \quad \text{(Equation 8)}$$

$$Y_3(x,y)=1/2\pi \int I(x,x,\Phi)(1+\xi\sin(\Phi))d\Phi \quad \text{(Equation 9)}$$

Computing device 104 additionally generates a first Fourier transform image by subtracting the first image, represented by $Y_1$ in Equation 7, from the second image, represented by $Y_2$ in Equation 8. Additionally, computing device 104 generates a second Fourier transform image by subtracting the first image, $Y_1$ in Equation 7, from the third image, $Y_2$ in Equation 9. The first Fourier transform image, $F_c$, is represented by Equation 10 and the second Fourier transform image, $F_s$, is represented by Equation 11, below.

$$Fc(x,y)=Y2(x,y)-Y1(x,y)=\xi/2\pi \int I(x,x,\Phi)\cos(\Phi)d\Phi \quad \text{(Equation 10)}$$

$$Fs(x,y)=Y3(x,y)-Y1(x,y)=\xi/2\pi \int I(x,x,\Phi)\cos(\Phi)d\Phi \quad \text{(Equation 11)}$$

Computing device 104 additionally generates a phase image, P, according to Equation 12, below.

$$P(x,y)=\arctan(Fs(x,y)/Fc(x,y)) \quad \text{(Equation 12)}$$

Figure 6:
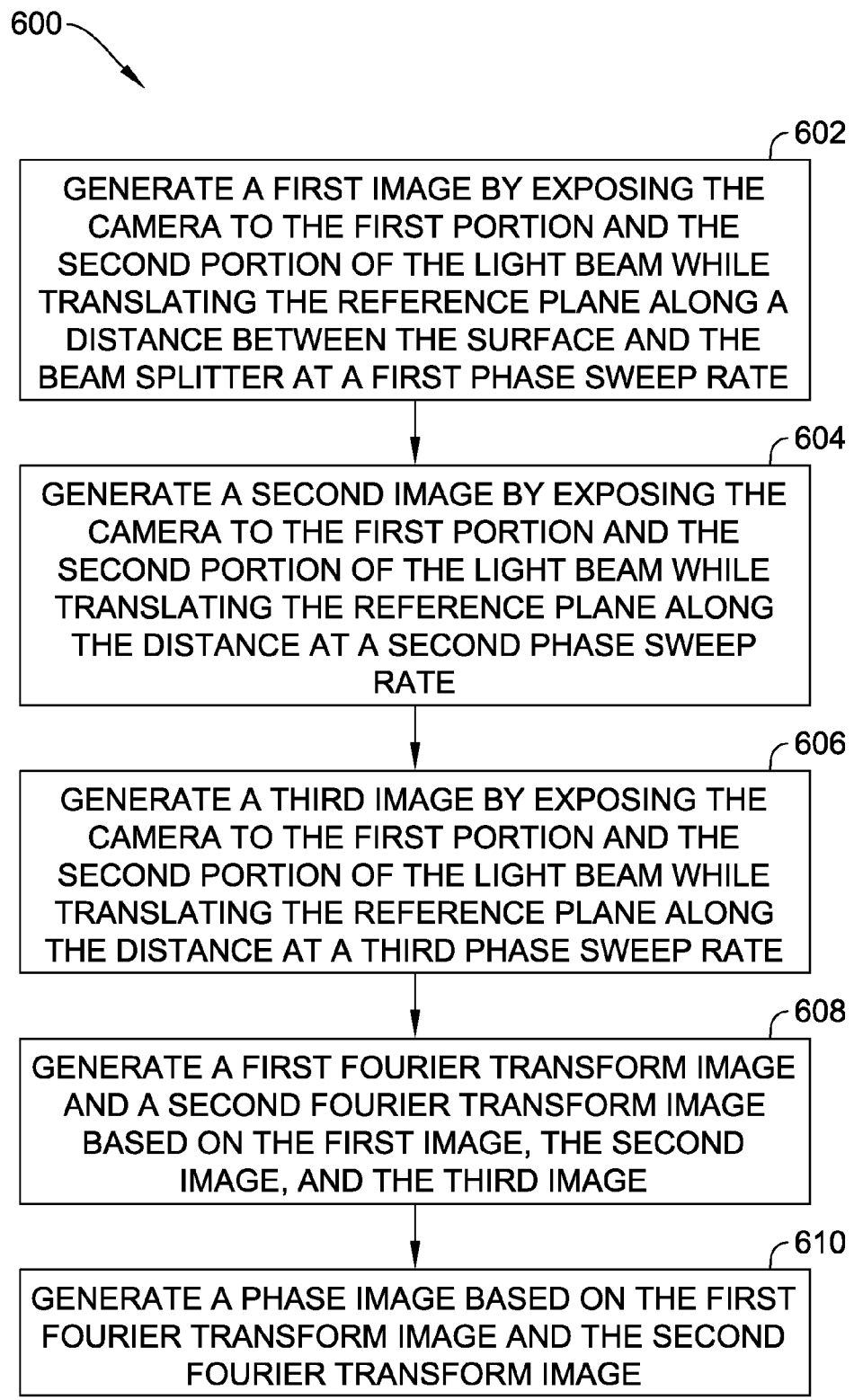
FIG. 6 is a flowchart of an example process that may be implemented by the system of FIG. 1 for measuring phase shift to detect irregularities on a surface.

FIG. 6 is a flowchart of an example process that may be implemented by system 100 (FIG. 1) for measuring phase shift to detect irregularities on a surface. First, system 100 generates 602 a first image by exposing 102 camera to first portion 116 and second portion 118 of light beam 114 while translating reference plane 110 along a distance 120 between surface 108 and beam splitter 112 at a first phase sweep rate. Next, system 100 generates 604 a second image by exposing camera 102 to first portion 116 and second portion 118 of light beam 114 while translating reference plane 110 along distance 120 at a second phase sweep rate. Next, system 100 generates 606 a third image by exposing camera 102 to first portion 116 and second portion 118 of light beam 114 while translating reference plane 110 along distance 120 at a third phase sweep rate. Next, system 100 generates 608 a first Fourier transform image and a second Fourier transform image based on the first image, the second image, and the third image. Next, system 100 generates 610 a phase image based on the first Fourier transform image and the second Fourier transform image. In some implementations, computing device 104 performs one or more of steps 602-610. As described above, in some implementations, computing device 104 is included within camera 102.

In an example implementation, camera 102 may include an analog to digital converter with a resolution of approximately 0.037 degrees and may allocate 12 bits to each pixel value. Further, computing device 104 may adjust pixel values such that the first image, $Y_1$, has pixel values at about 2048. With the modulation coefficient at approximately 0.75, the digitizing error is at most 0.0373°, as shown in Equation 13.

$$\text{Digitizing error} \le \tan^{-1}(0.75*2048)=0.0373° \quad \text{(Equation 13)}$$

In subtracting the first image from the second image to generate the first Fourier transform image, and subtracting the first image from the third image to generate the second Fourier transform image, erroneous pixel values (i.e., "hot pixels") are cancelled out. More specifically, hot pixel intensity offset is determined by exposure time only. Given that all three exposures have the same exposure time, hot pixels are cancelled out during generation of the first Fourier transform image and the second Fourier transform image.

A technical effect of systems and methods described herein includes at least one of: (a) generating a first image by exposing a camera to a first portion and a second portion of a light beam while translating a reference plane along a distance between a surface and a beam splitter at a first phase sweep rate; (b) generating a second image by exposing the camera to the first portion and the second portion of the light beam while translating the reference plane along the distance at a second phase sweep rate; (c) generating a third image by exposing the camera to the first portion and the second portion of the light beam while translating the reference plane along the distance at a third phase sweep rate; (d) generating, by a computing device, a first Fourier transform image and a second Fourier transform image based on the first image, the second image, and the third image; and (e) generating, by the computing device, a phase image based on the first Fourier transform image and the second Fourier transform image.

As compared to known systems and methods for performing interferometric phase measurement, the systems and methods described herein facilitate performing interferometric phase measurement with increased accuracy and speed. Accordingly, irregularities in the surface of an object may be detected faster and with improved reliability over previous systems and methods.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for measuring phase shift to detect irregularities of a surface, said method is implemented with a camera, a computing device coupled to or within the camera, a light source, a surface disposed opposite the light source, a semi-reflective reference plane disposed between the light source and the surface, and a beam splitter disposed between the light source and the reference plane, wherein the light source emits a light beam comprising a first portion and a second portion, wherein the first portion is reflected by the reference plane and the second portion is transmitted through the reference plane and reflected by the surface, wherein the beam splitter directs the reflected first portion and the reflected second portion to the camera, said method comprising the steps of:

generating a first image by exposing the camera to the first portion and the second portion of the light beam while translating the reference plane along a distance between the surface and the beam splitter at a first phase sweep rate;

generating a second image by exposing the camera to the first portion and the second portion of the light beam while translating the reference plane along the distance at a second phase sweep rate;

generating a third image by exposing the camera to the first portion and the second portion of the light beam while translating the reference plane along the distance at a third phase sweep rate;

generating, by the computing device, a first Fourier transform image and a second Fourier transform image based on the first image, the second image, and the third image; and generating, by the computing device, a phase image based on the first Fourier transform image and the second Fourier transform image.

2. The method of claim 1, wherein translating the reference plane along a distance further comprises translating the reference plane along a distance that corresponds to a phase sweep that is an integer multiple of 2*pi radians.

3. The method of claim 1, wherein generating the first Fourier transform image comprises subtracting the first image from the second image.

4. The method of claim 1, wherein generating the second Fourier transform image comprises subtracting the first image from the third image.

5. The method of claim 1, wherein generating the phase image comprises calculating an arctangent of the second Fourier transform image divided by the first Fourier transform image.

6. The method of claim 1, further comprising controlling the first phase sweep rate such that the first phase sweep rate is constant and the camera accumulates a first phase-dependent fringe intensity.

7. The method of claim 6, further comprising controlling the second phase sweep rate such that the camera accumulates a second phase-dependent fringe intensity that is equal to the first phase-dependent fringe intensity plus a first order cosine Fourier transform of the first phase-dependent fringe intensity.

8. The method of claim 6, further comprising controlling the third phase sweep rate such that the camera accumulates a third phase-dependent fringe intensity that is equal to the first phase-dependent fringe intensity plus a first order sine Fourier transform of the first phase-dependent fringe intensity.

9. A system for measuring phase shift to detect irregularities of a surface, said system comprising:
a camera;
a computing device coupled to or within the camera;
a light source;
a surface disposed opposite the light source;
a semi-reflective reference plane disposed between the light source and the surface; and
a beam splitter disposed between the light source and the reference plane, wherein the light source emits a light beam comprising a first portion and a second portion, wherein the first portion is reflected by the reference plane and the second portion is transmitted through the reference plane and reflected by the surface, wherein the beam splitter directs the reflected first portion and the reflected second portion to the camera, and wherein said system is configured to:
generate a first image by exposing the camera to the first portion and the second portion of the light beam while translating the reference plane along a distance between the surface and the beam splitter at a first phase sweep rate;
generate a second image by exposing the camera to the first portion and the second portion of the light beam while translating the reference plane along the distance at a second phase sweep rate;
generate a third image by exposing the camera to the first portion and the second portion of the light beam while translating the reference plane along the distance at a third phase sweep rate;

generate a first Fourier transform image and a second Fourier transform image based on the first image, the second image, and the third image; and
generate a phase image based on the first Fourier transform image and the second Fourier transform image.

10. The system of claim 9, wherein the surface is a surface of a wafer.

11. The system of claim 9, wherein said system is further configured to translate the reference plane along a distance by translating the reference plane along a distance that corresponds to a phase sweep that is an integer multiple of 2*pi radians.

12. The system of claim 9, wherein said system is further configured to generate the first Fourier transform image by subtracting the first image from the second image.

13. The system of claim 9, wherein said system is further configured to generate the second Fourier transform image by subtracting the first image from the third image.

14. The system of claim 9, wherein said system is further configured to generate the phase image by calculating an arctangent of the second Fourier transform image divided by the first Fourier transform image.

15. The system of claim 9, wherein said system is further configured to control the first phase sweep rate such that the first phase sweep rate is constant and the camera accumulates a first phase-dependent fringe intensity.

16. The system of claim 15, wherein said system is further configured to control the second phase sweep rate such that the camera accumulates a second phase-dependent fringe intensity that is equal to the first phase-dependent fringe intensity plus a first order cosine Fourier transform of the first phase-dependent fringe intensity.

17. The system of claim 15, wherein said system is further configured to control the third phase sweep rate such that the camera accumulates a third phase-dependent fringe intensity that is equal to the first phase-dependent fringe intensity plus a first order sine Fourier transform of the first phase-dependent fringe intensity.

18. A non-transitory computer-readable storage medium having computer-executable instructions embodied thereon for measuring phase shift to detect irregularities of a surface in a system including a camera, a computing device coupled to or within the camera, a light source, a surface disposed opposite the light source, a semi-reflective reference plane disposed between the light source and the surface, and a beam splitter disposed between the light source and the reference plane, wherein the light source emits a light beam comprising a first portion and a second portion, wherein the first portion is reflected by the reference plane and the second portion is transmitted through the reference plane and reflected by the surface, and wherein the beam splitter directs the reflected first portion and the reflected second portion to the camera, wherein when executed by the computing device, said computer-executable instructions cause the computing device to:
generate a first image by exposing the camera to the first portion and the second portion of the light beam while translating the reference plane along a distance between the surface and the beam splitter at a first phase sweep rate;
generate a second image by exposing the camera to the first portion and the second portion of the light beam while translating the reference plane along the distance at a second phase sweep rate;
generate a third image by exposing the camera to the first portion and the second portion of the light beam while translating the reference plane along the distance at a third phase sweep rate;

generate a first Fourier transform image and a second Fourier transform image based on the first image, the second image, and the third image; and generate a phase image based on the first Fourier transform image and the second Fourier transform image.

19. The non-transitory computer-readable storage medium of claim 18, further comprising computer-executable instructions that, when executed by the computing device, cause the computing device to translate the reference plane along a distance by translating the reference plane along a distance that corresponds to a phase sweep that is an integer multiple of 2*pi radians.

20. The non-transitory computer-readable storage medium of claim 18, further comprising computer-executable instructions that, when executed by the computing device, cause the computing device to generate the first Fourier transform image by subtracting the first image from the second image and to generate the second Fourier transform image by subtracting the first image from the third image.

* * * * *